(12) United States Patent
  Wong

(10) Patent No.: US 8,097,856 B2
(45) Date of Patent: Jan. 17, 2012

(54) SUPER-MINIATURIZED NDIR GAS SENSOR

(75) Inventor: Jacob Y Wong, Goleta, CA (US)

(73) Assignee: Airware, Inc., Goleta, CA (US)

(*) Notice: Subject to any disclaimer, the term of this patent is extended or adjusted under 35 U.S.C. 154(b) by 0 days.

(21) Appl. No.: 13/100,223

(22) Filed: May 3, 2011

(65) Prior Publication Data

US 2011/0204236 A1    Aug. 25, 2011

Related U.S. Application Data

(63) Continuation-in-part of application No. 12/859,749, filed on Aug. 19, 2010.

(60) Provisional application No. 61/331,327, filed on May 4, 2010, provisional application No. 61/274,874, filed on Aug. 21, 2009.

(51) Int. Cl.
  *G01N 21/35* (2006.01)
(52) U.S. Cl. ........................................ 250/345; 250/343
(58) Field of Classification Search .................. 250/345, 250/343
  See application file for complete search history.

(56) References Cited

U.S. PATENT DOCUMENTS

| | | | |
|---|---|---|---|
| 3,793,525 A | 2/1974 | Burch et al. | |
| 3,811,776 A | 5/1974 | Blau, Jr. | |
| 4,578,762 A | 3/1986 | Wong | |
| 4,694,173 A | 9/1987 | Wong | |
| 5,163,332 A | 11/1992 | Wong | |
| 5,444,249 A | 8/1995 | Wong | |
| 5,689,114 A * | 11/1997 | Miyazaki et al. | 250/343 |
| 6,075,246 A * | 6/2000 | Stock | 250/343 |
| 6,753,967 B2 * | 6/2004 | Stuttard | 356/437 |
| 6,762,410 B1 * | 7/2004 | Wiechers et al. | 250/343 |
| 2008/0185524 A1 * | 8/2008 | Kanstad | 250/338.5 |

* cited by examiner

*Primary Examiner* — Constantine Hannaher
(74) *Attorney, Agent, or Firm* — Wagner, Anderson and Bright, P.C.; Roy L. Anderson

(57) ABSTRACT

Two detector elements are optically isolated by having them mounted (die-attached) on the same header so that the thermal tracking of the detectors respectively for the signal and reference channels is close to ideal. Furthermore, such an optical isolation technique or cross-interference suppression between the two detector elements mounted on the same header also allows the use of only one and the same narrow band pass interference filter covering both detectors. Thus the thermal tracking of the filters respectively for the signal and reference channels is also close to perfection as both channels share the same filter.

6 Claims, 3 Drawing Sheets

SUPER-MINIATURIZED NDIR GAS SENSOR

CROSS-REFERENCE TO RELATED APPLICATIONS

The present application claims the priority benefit of U.S. Ser. No. 61/331,327, filed May 4, 2010, the disclosure of which is specifically incorporated herein by reference. This application is also a continuation-in-part of U.S. Ser. No. 12/859,749, filed Aug. 19, 2010, the disclosure of which is specifically incorporated herein by reference, which itself claimed the priority benefit of U.S. Ser. No. 61/274,874, filed Aug. 21, 2009, the disclosure of which is also specifically incorporated herein by reference.

FIELD OF THE INVENTION

The present application is in the field of gas analysis, and specifically relates to apparatus using a Non-Dispersive Infrared (NDIR) gas analysis technique to determine the concentration of a particular type of gas present in a chamber by sensing the absorption of infrared radiation passing through the gas.

BACKGROUND OF THE INVENTION

The Non-Dispersive Infrared ("NDIR") technique has long been considered as one of the best methods for gas measurement. In addition to being highly specific, NDIR gas analyzers are also very sensitive, stable, reliable and easy to maintain and service. Ever since the NDIR technique of gas measurement was first introduced and practiced in the mid 1950's, a large number of improved measurement techniques based upon the NDIR principle for gas detection have been proposed and successfully demonstrated. The most notable advances over the years in this field are summarized as follows.

Burch et al. (U.S. Pat. No. 3,793,525) and Blau et al. (U.S. Pat. No. 3,811,776) in 1974 were the first to advance a so-called "Double Beam" technique for NDIR gas measurement by taking advantage of the principle of nonlinear absorption for some strongly absorbing gases such as $CO_2$ to create a reference channel. Shortly thereafter, this "Double Beam" NDIR gas sensor technique was greatly simplified with the use of two interposed spectral filters (one absorbing and one neutral) to create a sample and a reference detector channel. Subsequent NDIR gas sensors, designed using this technique, have enjoyed good performance alluded to briefly above.

In U.S. Pat. No. 4,578,762 (1986) Wong advanced the first self-calibrating NDIR $CO_2$ analyzer using a novel two-wheel chopper and mirror arrangement. Another improved type of such gas analyzer is shown and described in U.S. Pat. No. 4,694,173 (1987) by Wong. This gas sensor has no moving parts for effecting the interposition of spectral filters to create both a sample and reference detector channel as in the NDIR gas analyzers described earlier.

In U.S. Pat. No. 5,163,332 (1992), Wong advanced the so-called "wave-guide" sample chamber concept for simplifying NDIR gas sensors into ones that are compact, rugged and low-cost while still maintaining their superior performance characteristics. This concept has subsequently been widely adopted in the design of today's NDIR gas sensors, particularly in low-cost and high volume versions.

All of the NDIR gas analyzers described above for the measurement of the concentrations of one or more gases in a mixture perform well functionally and have contributed successfully to the overall technical advancement in the field of gas analysis during the past two decades. They have been widely accepted in both the medical and industrial communities. Despite their undisputed success over the years, there still remain a number of important sensor performance characteristics that need to be greatly improved in order to further extend the useful applications of these devices in a number of areas.

By far the most deficient performance characteristic of gas sensors of today, inclusive of NDIR gas sensors, is the sensor output stability over time. Unlike the temperature controller or thermostat device which just about everybody is familiar with at home or in their workplaces for sensing temperature that never requires output adjustment or recalibration over time, such is not the case for gas sensors irrespective of their operational principle, functional design, material construct or even costs. Dependent upon the type of gas sensors, just about every one of them requires recalibration once every six months to a year without exception in order that they remain accurate over time. While this performance deficiency has been well tolerated over the years, it remains as a significant drawback for gas sensors and even precludes their use in a number of vital applications and therefore there has been a long-felt need for elimination of this problem.

The second most prominent performance deficiency for gas sensors of today irrespective of their operational principle is their output dependence as a function of the temperature of the environment wherein the sensors are located. This performance deficiency for just about all gas sensors is universally, albeit reluctantly, dealt with by specifying the output correction per degree of temperature change with respect to the output stipulated at a standard temperature. In some gas sensors these output temperature corrections are quite large and in many cases severely limit the use of these sensors outdoors. It would be a significant step forward in the development of future gas sensors, particularly for the NDIR type, because of its prevalent use in most industries, that this performance deficiency be also overcome and, again, there has been a long-felt need for overcoming this problem.

The afore-mentioned serious NDIR gas sensor performance deficiencies, namely sensor output drift over time and output dependency as a function of exposed sensor temperature, have earlier been addressed by the present inventor in a provisional patent application 61/274,874 to the US Patent Office filed on Aug. 21, 2009 and entitled "Absorption Biased NDIR Gas Sensing Methodology." In this recent patent disclosure, the present inventor takes advantage of the fact that if the spectral content of radiation from the source and/or convoluted with those from the surroundings be always kept the same for both the reference and the signal channels of an NDIR gas sensor, assuming that this sensor uses the most widely deployed dual-channel methodology, the output of the sensor taken as the ratio of the signal output over the reference output can always be kept constant or unchanged over time except when the gas of interest is present in the sample chamber.

In order that this recently disclosed Absorption Biased methodology be implemented, both the signal and the reference channel must be provided with exactly the same spectral narrow band pass filter designed for detecting the gas of interest in front of the respective infrared detectors. In order to differentiate between the signal and the reference channel outputs from the respective detectors in the presence of the gas of interest, an absorption bias is designed between the two channels via the use of different sample chamber path lengths for the two channels. Thus, if the sample chamber path length for the signal channel is longer than that for the reference channel, the signal channel detector output will change greater (or be reduced more) than that for the reference channel when the same concentration level of the gas of interest is present in the sample chamber. In other words, the sensor output will change as the concentration level of the gas of interest changes in the sample chamber as reflected by the calibration curve which can be prepared for the sensor.

The fact that both detection channels have the same narrow band pass spectral filter and they receive radiation from one and the same single infrared source as taught by the widely deployed dual-channel NDIR gas detection methodology, they are all affected in the same way to first order when there are spectral changes caused by temperature variations in the sample chamber and/or by the short or long-term operational changes (e.g. aging) of the infrared source. Thus the outputs of the dual-channel NDIR gas sensor for the detection of any gas of interest implemented using the inventor's recently disclosed Absorption Biased methodology will stay virtually drift-free over time without the need for any periodic re-calibration or software correction.

While the Absorption Biased NDIR gas sensor methodology as disclosed recently by the present inventor adequately addresses the serious deficiencies of output instability over time and dependence of sensor temperature for presently deployed dual-channel NDIR gas sensors, two other important performance characteristics for these sensors, namely miniaturization and lowest possible unit cost, have still not been taken into consideration. Electrochemical gas sensors have long been considered to be small and low cost, but their performances are also known to suffer from output instability over time and relatively short operating lives when compared to other non-electrochemical gas sensors, particularly the NDIR types. Over the past several years, the advent of MEMS (Micro Electro-Mechanical System) sensors of all types have steadfastly driven the available sensor sizes drastically downwards. However, such a promising sensor technology with its own limitations has yet to penetrate into the domain of NDIR gas sensors. The requirements for stable infrared sources and detectors along with physically long path length sample chambers in order to detector very low concentration of interested gases are still impediments for the MEMS technology to overcome in the future.

The realization of NDIR gas sensor miniaturization achieving concomitantly the lowest possible unit sensor cost has long been the goal of many R&D engineers working in this field. Over a decade ago, Wong disclosed in U.S. Pat. No. 5,444,249 (Aug. 22, 1995) a miniaturized NDIR gas sensor manufactured using semiconductor micro-machining techniques from a semiconductor material such as Si or GaAs. The NDIR gas sensor comprises an optical waveguide, a light source at one end of the waveguide, at least one light detector at the end of the waveguide opposite the light source. A diffusion type gas sample chamber is formed within the waveguide and interposed in the optical path between the light source and the light detector. The light source and light detector, with a separate band pass filter interposed between them, are thermally isolated from the waveguide which acts as the gas sample chamber for the sensor. Since the NDIR sensor is fabricated out of a semiconductor material, the source driver and signal processing electronics can be added directly to the sensor using integrated circuit fabrication techniques. Unfortunately, such a proposed miniaturized NDIR gas sensor is only a single-channel device whose performance is far inferior to the present-day deployed dual-channel sensors even before their deficiencies are remedied by the recently disclosed Absorption Biased technique.

From the above discussion, it is quite apparent that the recently disclosed Absorption Biased methodology for NDIR gas sensors can further be improved with an innovative approach for miniaturization and a concomitant realization of achieving a lower unit cost for such a sensor.

SUMMARY OF THE INVENTION

The present invention is generally directed to an NDIR gas sensor and methodology in which an absorption bias between signal and reference outputs are used to determine sample concentration of a gas being measured. The absorption bias is created by using a signal channel with a path length that is greater than a path length of a reference channel in the sample chamber while both the signal and reference detectors use an identical narrow band pass filter in a single detector package and cross talk between the signal and output detectors is minimized.

In a first, separate group of aspects of the present invention, the narrow band pass filter is mounted in close proximity to top surfaces of the reference and signal detectors which can be mounted (die-attached) to a header housing, the two detectors share a common thermal platform that can also be shared by the sample chamber and the infrared source and each of the reference and signal channels can be light tunnels.

It is therefore a primary object of the present invention to advance an improved design for an NDIR gas sensor and methodology which improves upon the Absorption Based methodology for NDIR gas sensors disclosed previously.

This and further objects and advantages will be apparent to those skilled in the art in connection with the drawings and the detailed description of the inventions set forth below.

DETAILED DESCRIPTION OF THE INVENTION

Figure 1:
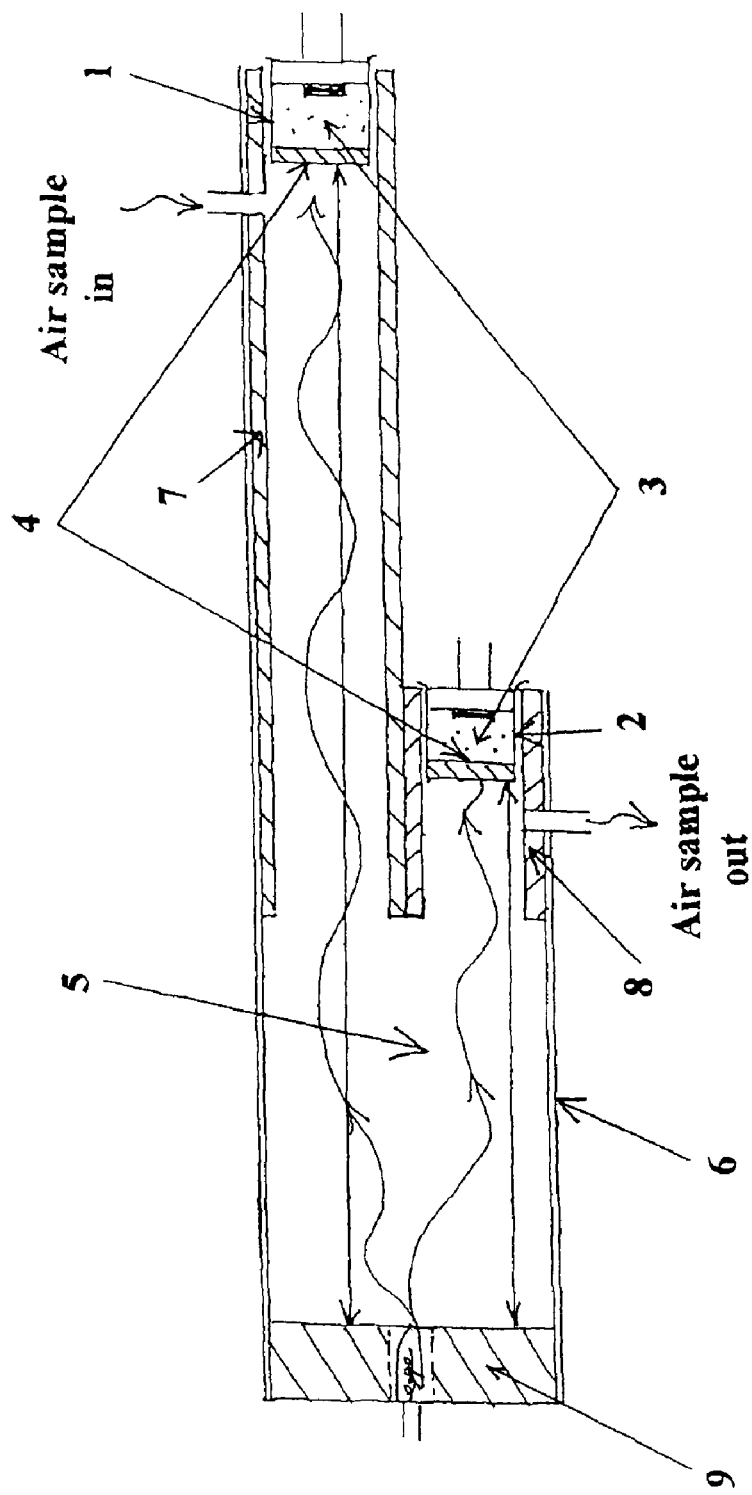
FIG. 1 depicts the schematic components layout of an earlier disclosed Absorption Biased NDIR gas sensing methodology.

FIG. 1 depicts the optical components layout disclosed in U.S. Ser. No. 12/859,749 for the Absorption Biased methodology for NDIR gas sensors. As shown in FIG. 1, both the signal channel detector 1 and the reference channel detector 2 are entrapped with 100% nitrogen 3 and have the same narrow band pass spectral filter 4 which is used to detect the gas of interest in the sample chamber 5. As an example, the filter designed to be used for the detection of $CO_2$ gas would have a Center Wavelength (CWT)=$4.26\mu$ and a spectral Full Width half Maximum (FWHM)=$0.14\mu$. Notice that both detectors 1 and 2 are thermally connected to the entire sensor body 6 through their respective waveguides 7 and 8 and consequently they always share the same thermal platform with each other. In other words, the entire sensor body 6 which is in essence a composite of aluminum parts comprising the infrared source mount 9, sample chamber 5 and the waveguides 7 and 8 respectively for the signal and reference channels, provides an excellent common thermal platform for detectors 1 and 2.

It is an object of the current invention to implement the Absorption Biased methodology for NDIR gas sensors with an innovative approach so as to simplify the overall sensor configuration by both the reduction of sensor layout dimensions and also the number of needed components. In so doing not only the sensor miniaturization objective is accomplished but also the overall sensor cost is reduced.

The Absorption Biased methodology for NDIR gas sensors follows the general design principle of a dual-channel implementation, namely a signal and a reference channel working in synchronism. Although it is taught that both the signal and the reference detectors for the two channels have to have exactly the same narrow band pass spectral filter and receive infrared radiation from one single and the same source, two standalone detectors with their respective identical spectral filters have to be implemented. It is further taught that in order for the methodology to work properly, the two separate detectors, with their individual detector element and identical spectral filter must share a common thermal platform. This is because the individual spectral filters are extremely temperature sensitive and in order for the methodology to work, these components must track in temperature at all times.

The present invention advances an innovative way of optically isolating two detector elements mounted (die-attached) on the same header so that the thermal tracking of the detectors respectively for the signal and reference channels is close to ideal. Furthermore, such an optical isolation technique or cross-interference suppression between the two detector elements mounted on the same header also allows the use of only one and the same narrow band pass interference filter covering both detectors. Thus the thermal tracking of the filters respectively for the signal and reference channels is also close to perfection as both channels share the same filter.

The present invention therefore is able to reduce the number of detector packages needed from two to one and concomitantly the need for two separate narrow band pass filters from two to one. Such a component reduction, in addition to drastically improving the performance of the sensor, also has a rather big impact in reducing the production cost for the sensor. Furthermore, the current invention also introduces innovative use of extremely small diameter aluminum waveguides as the sample chamber for the sensor thereby reducing the physical dimensions for the sensor in its implementation.

Figure 2:
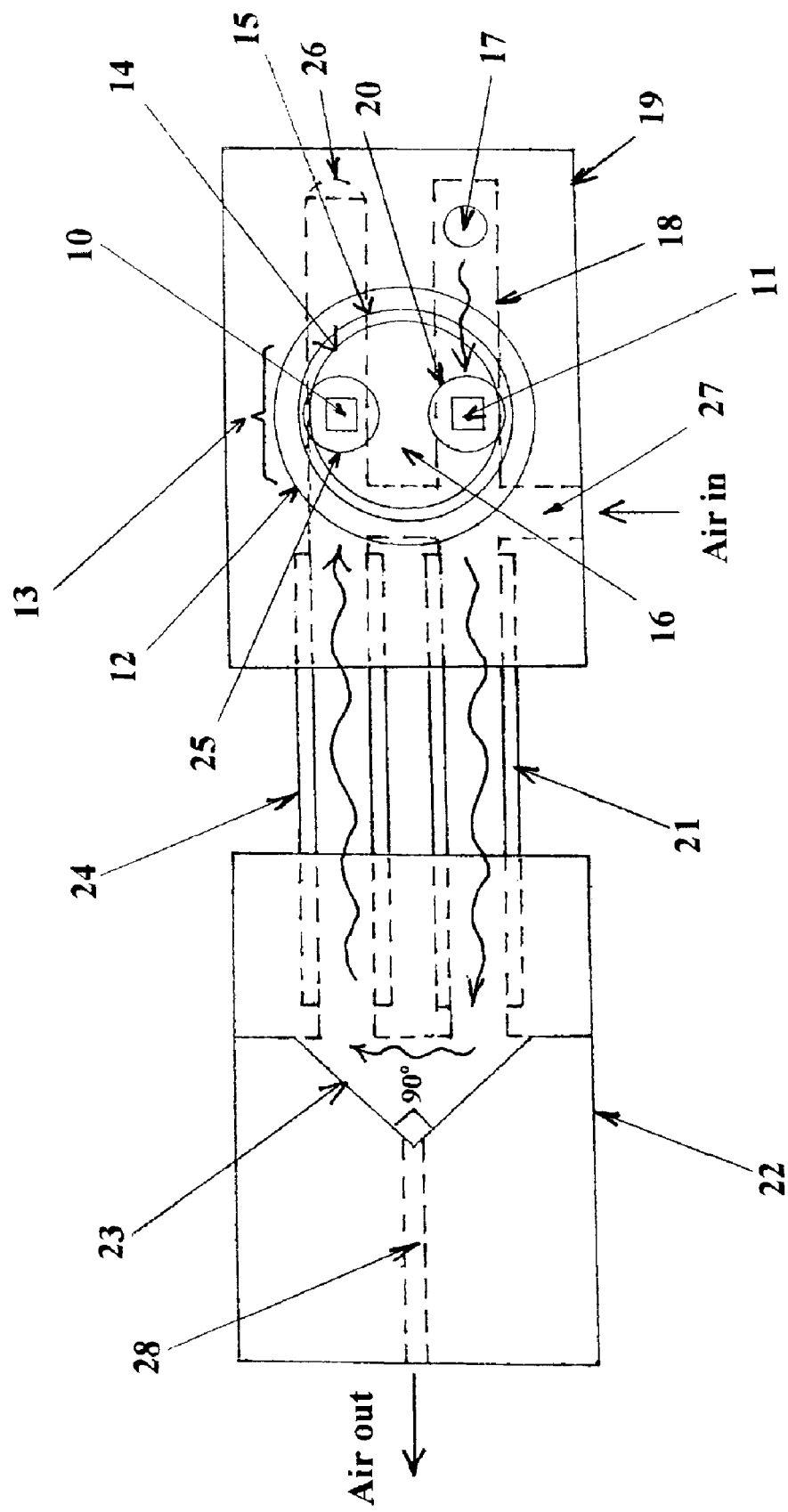
FIG. 2 depicts the schematic layout of the currently invented Super-Miniaturized NDIR gas sensing methodology.

FIG. 2 depicts the optical component layout for the current invention of a super-miniaturized NDIR gas sensor. As shown in FIG. 2, the signal channel detector 10 and the reference channel detector 11 are mounted (die-attached) on the same header 12 of a TO-18 detector package 13 having a diameter of ~0.2". A narrow band pass filter 14 possessing the spectral characteristics for detecting the gas of interest is mounted on the TO-18 can 15 forming with the header a hermetically sealed detector package 13 entrapping 100% nitrogen gas 16 inside. Radiation from a miniaturized light source 17 (diameter ~0.090") emanates from one end of the waveguide sample chamber 18 formed inside an aluminum block 19 which houses both the light source 17 and the detector packaging 13. Radiation from source 17 reaches the reference channel detector 11 via a vertical light tunnel 20 formed inside the aluminum block 19 and continues along an external waveguide 21. By connecting itself to the aluminum block 19 with another aluminum block 22, waveguide 21 forms a continuation of the sensor sample chamber.

Radiation propagating inside waveguide 21 changes its direction 180° by a right-angle mirror 23 formed inside the aluminum block 22 and continues propagating along another waveguide 24 which also serves to connect blocks 19 and 22. The radiation emanating originally from light source 17 finally reaches the signal channel detector 10 via another vertical light tunnel 25 before being removed by a light absorber 26. Notice that ambient air to be sampled enters the sensor sample chamber via duct 27 in the aluminum block 19 and exits via duct 28 in aluminum block 22.

A closer examination of FIG. 2 reveals the fact this optical component layout for the currently invented super-miniaturized NDIR gas sensor closely resembles that for the earlier disclosed Absorption Biased methodology as shown in FIG. 1. The main difference between the two layouts is the combination of both the signal channel detector and the reference channel detector into a single unit thereby reducing the number of detector packages from two to one. This not only reduces greatly the sensor dimensions but it also reduces the number of spectral filters from two to one since there is only one detector package and both detector channels can now share the same spectral filter. The fact that only one detector package needs to be deployed also greatly reduces the sensor cost in addition to enabling the thermal tracking of the key components, namely the detectors and the spectral filters, to be accomplished in a most optimum manner.

The mounting of two individual detector elements in close proximity to each other on a common header can introduce very serious signal cross-interference effects if care is not taken to alleviate such a precarious situation. The effect of such a possible deleterious consequence is minimized by an innovative arrangement of the critical components for the sensor as depicted in FIG. 3.

Figure 3:
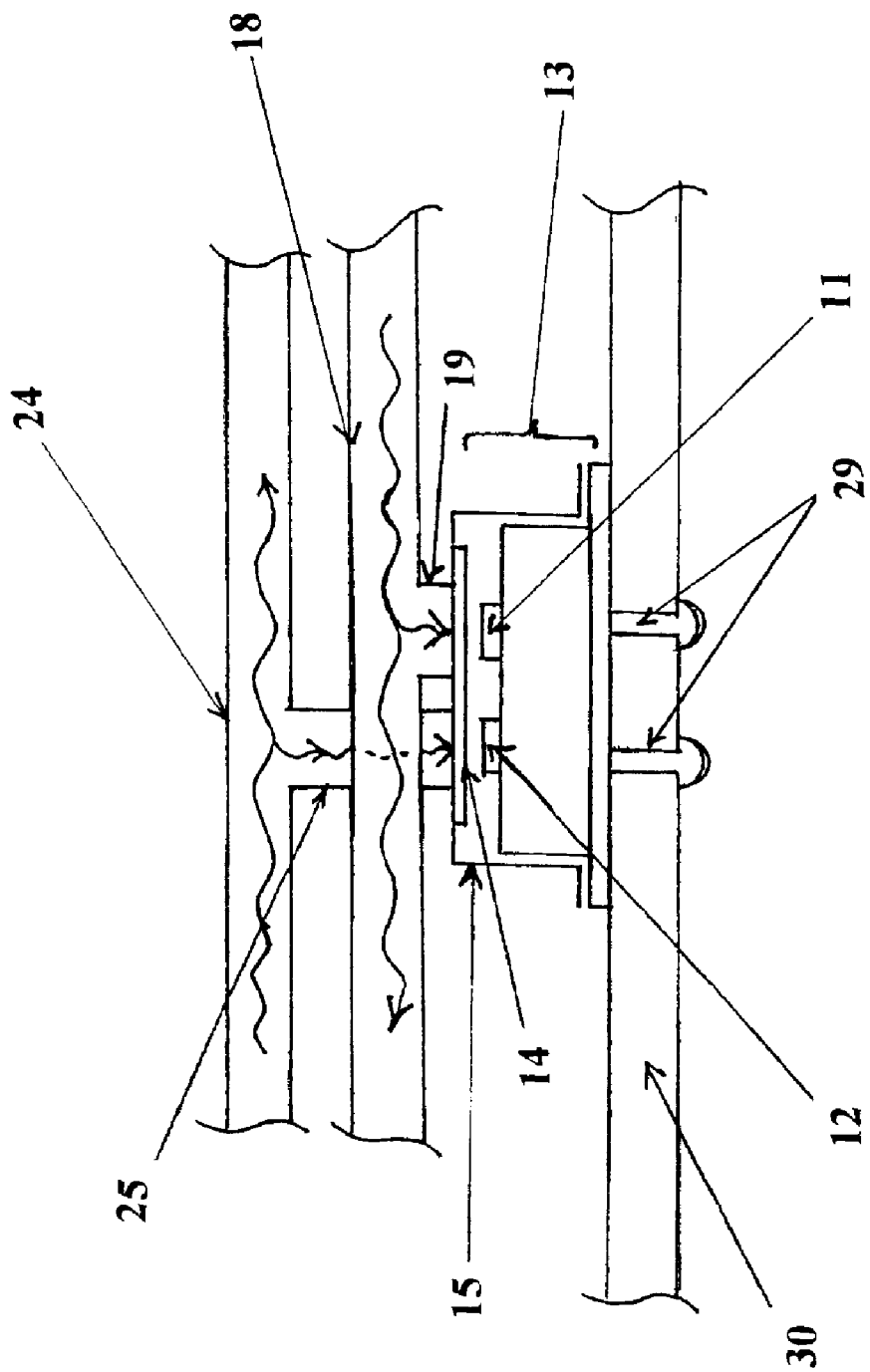
FIG. 3 depicts the detailed schematic layout in the vicinity of the detector package showing how the signal cross-talks between the two closely die-attached detector elements on the same header are greatly suppressed.

In FIG. 3, the leads 29 of the detector package 13 (see FIG. 2) are shown soldered to the printed circuit board (PCB) 30. Radiation emanating from the light source (not shown in FIG. 3) along a waveguide 18 (see FIG. 2) is scattered downwards through a light tunnel 19 (see FIG. 2) onto first the spectral filter 14 and then the reference channel detector element 11 (see FIG. 2). Similarly, radiation propagating along the sensor sample chamber after making a 180° directional change and continuing along waveguide 24 (see FIG. 2) is scattered downwards through another light tunnel 25 (see FIG. 2) onto first the same spectral filter 14 and then the signal channel detector element 12 (see FIG. 2). In such an optical arrangement, it is paramount that the spectral filter 14 mounted on the detector can 15 is installed extremely close (<0.25 mm) to the top surfaces of the detector elements 11 and 12. The combination of the radiation being funneled down separately through different light tunnels onto the respective detector elements and the fact that the spectral filter is physically installed as close as is feasible to the detector elements themselves serves to minimize significantly any signal cross-talks between them.

While the invention has been described herein with reference to a preferred embodiment, this embodiment has been presented by way of example only, and not to limit the scope of the invention. Additional embodiments thereof will be obvious to those skilled in the art having the benefit of this detailed description. Further modifications are also possible in alternate embodiments without departing from the inventive concept.

Accordingly, it will be apparent to those skilled in the art that still further changes and modifications in the actual concepts described herein can readily be made without departing from the spirit and scope of the disclosed inventions.

What is claimed is:

1. A Non-Dispersive Infrared ("NDIR") gas sensor for detecting the presence of a chosen gas, comprising:
   a single infrared source for generating infrared radiation;
   a sample chamber having a signal channel path length and a reference channel path length, the signal channel path length being greater than the reference path length;

electronics for determining a sample concentration of the chosen gas;
a single detector package, comprising:
   a narrow band pass filter mounted in the single detector package;
   a reference detector that produces a reference output, said reference detector being mounted in the single detector package such that the narrow band pass filter lies in between a reference detector light path from the infrared source to the reference detector, a reference top surface of the reference detector being mounted in close proximity to the narrow band pass filter; and
   a signal detector that produces a signal output, said signal detector being mounted in the single detector package such that the narrow band pass filter lies in between a signal detector light path from the infrared source to the signal detector, a signal top surface of the signal detector being mounted in close proximity to the narrow band pass filter;
a reference light tunnel for funneling infrared radiation from the reference channel path length onto the reference detector; and
a signal light tunnel for funneling infrared radiation from the signal channel path length onto the signal detector;
wherein the reference light tunnel is physically separate from the signal light tunnel so that infrared radiation traveling through either the reference light tunnel or the signal light tunnel will not pass into the other tunnel as it is traveling through its own tunnel;
wherein the signal channel path length is sufficiently greater than the reference channel path length so that the electronics can use an absorption bias between the signal output and the reference output to determine the chosen gas concentration in the sample chamber by using the reference output and the signal output obtained solely from use of the single infrared source; and
wherein the single infrared source is the only source of infrared radiation emitted into the sample chamber.

2. The NDIR gas sensor of claim 1, wherein the reference and signal detectors are mounted to a single header housing.

3. The NDIR gas sensor of claim 1, wherein the reference detector and the signal detector both detect infrared radiation generated from the infrared source at the same time.

4. A process for determining a sample concentration of a chosen gas in a sample chamber of a Non-Dispersive Infrared ("NDIR") gas sensor, comprising:
   emitting infrared radiation from a single infrared source into a sample chamber having both a signal channel path length and a reference channel path length, the signal channel path length being greater than the reference path length;
   funneling infrared radiation from the reference channel path length through a reference light pipe to a reference detector that produces a reference output;
   funneling infrared radiation from the signal channel path length through a signal light pipe to a signal detector that produces a signal output;
   using electronics to determine the sample concentration by use of an absorption bias created between the signal output and the reference output due to the difference in lengths between the signal channel path length and the reference channel path length, said determination being made by using the reference output and the signal output obtained solely from use of the single infrared source;
   wherein both the reference detector and the signal detector are mounted in close proximity to a narrow band pass filter; and
   wherein the reference detector, the signal detector and the narrow band pass filter are mounted in a single detector package.

5. The process of claim 4, wherein the reference and signal detectors are mounted to a single header housing.

6. The process of claim 4, wherein the reference detector and the signal detector both detect infrared radiation generated from the infrared source at the same time.

\* \* \* \* \*